(12) United States Patent
Keller

(10) Patent No.: US 6,217,619 B1
(45) Date of Patent: Apr. 17, 2001

(54) ENDOPROSTHESIS FOR A LEAST PARTIAL REPLACEMENT OF A TIBIA

(75) Inventor: Arnold Keller, Kayhude (DE)

(73) Assignees: GMT Gesellschaft für medizinische Technik mbH; Waldemar Link GmbH & Co. KG, both of Hamburg (DE)

( * ) Notice: Subject to any disclaimer, the term of this patent is extended or adjusted under 35 U.S.C. 154(b) by 0 days.

(21) Appl. No.: 09/205,664

(22) Filed: Dec. 4, 1998

(30) Foreign Application Priority Data

Dec. 5, 1997 (DE) .............................................. 197 54 079

(51) Int. Cl.$^7$ ....................................................... A61F 2/38
(52) U.S. Cl. ...................... 623/20.34; 623/20.14
(58) Field of Search .............................. 623/20.14, 20.15, 623/20.21, 20.32, 20.34

(56) References Cited

U.S. PATENT DOCUMENTS

| 4,268,920 | * | 5/1981 | Engelbrecht et al. | 623/20 |
| 4,865,606 | * | 9/1989 | Rehder | 623/20 |
| 5,268,000 | * | 12/1993 | Ottieri et al. | 623/20 |

* cited by examiner

Primary Examiner—David J. Isabella
(74) Attorney, Agent, or Firm—Henry M. Feiereisen

(57) ABSTRACT

An endoprosthesis for replacing at least part of a tibia, includes an elongate shaft extending longitudinally in the direction of a lower leg and having an upper end facing a knee joint and a lower end facing a natural talus. An endoprosthetic knee joint having a tibial plateau is secured to the upper end of the shaft. The talus supports a coupling portion which is connected to the lower end of the shaft.

19 Claims, 2 Drawing Sheets

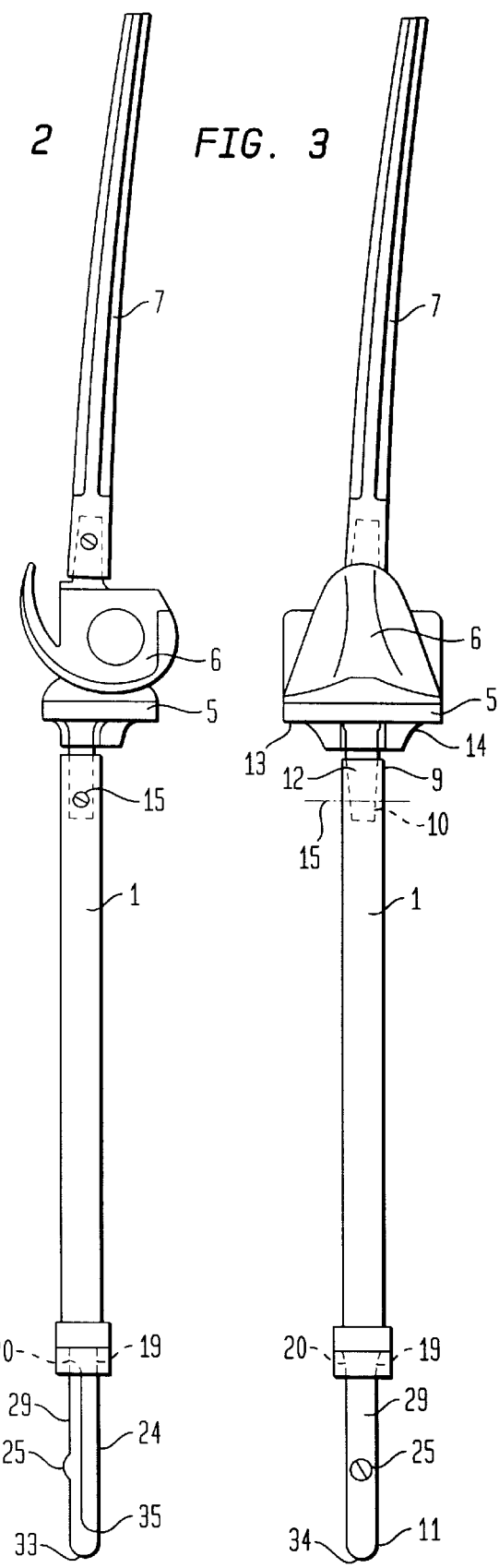
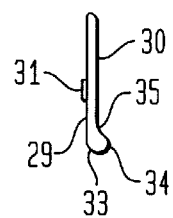
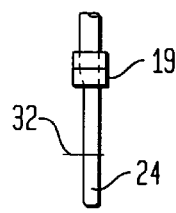
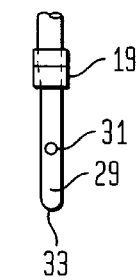
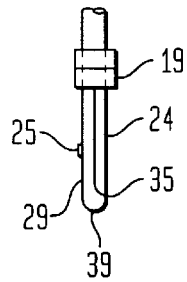
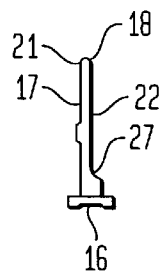
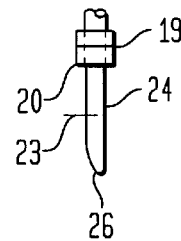
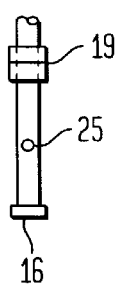
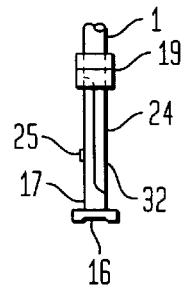

ENDOPROSTHESIS FOR A LEAST PARTIAL REPLACEMENT OF A TIBIA

CROSS-REFERENCES TO RELATED APPLICATIONS

This application claims the priority of German Patent Application Serial No. 197 54 079.1, filed Dec. 5, 1997, the subject matter of which is incorporated herein by reference.

BACKGROUND OF THE INVENTION

The present invention generally relates to an endoprosthesis for replacing at least part of the tibia.

After carrying out, for example, a complicated tumor resection or after encountering a failure in the anchoring of a replacement knee prosthesis, substantial problems may arise in the area of the tibia when forces are transmitted from the knee joint to the ankle joint. In particular, it is conceivable that portions of the tibia must be resected, without any possibility to connect the bone components between which the resected portions are removed. In these situations, amputations are frequently the only option.

SUMMARY OF THE INVENTION

It is thus an object of the present invention to provide an improved endoprosthetic implant, obviating the afore-stated drawbacks.

In particular, it is an object of the present invention to provide an improved endoprosthesis for situations requiring removal of parts of the tibia or the entire tibia or in which existent tibia parts do not exhibit a sufficient strength for realizing a force transmission, with resorting to amputation.

These objects, and others which will become apparent hereinafter, are attained in accordance with the present invention by providing an elongate shaft which extends longitudinally in direction of a lower leg and has an upper end facing a knee joint and a lower end facing a natural ankle joint, an endoprosthetic knee joint having a tibial plateau secured to the upper end of the shaft, and a coupling portion supported by the ankle joint and linked to the lower end of the shaft.

Such an endoprosthesis can be successfully implanted in situations where a portion of the tibia is either completely missing or so weakened as to be insufficient to transmit forces. In these cases, the shaft is utilized as a replacement for the tibia. This shaft may extend along the entire length or only partially through the tibia, if portions thereof are still existent. In this case, soft parts such as ligaments, tendons and muscles required to carry out motions have grown onto bony material that covers the shaft.

According to a preferred embodiment of the present invention, the shaft is formed as round rod, with a recess being provided on the upper end of the shaft for engagement by a pin which is fastened to the tibial plateau and secured in the recess. This type of embodiment allows the use of conventional endoprosthetic knee joints; however, in which accordance with the present invention, the pin on the tibial component is, unlike in conventional embodiments, not anchored directly in the tibial bone but in the shaft that completely or partially replaces the tibial bone. By anchoring the pin, which is made of steel, in a mating recess of the shaft which is also made of steel, relatively high forces can be transmitted while still enabling to provide the endoprosthesis with mutually guiding parts that exhibit comparably small dimensions.

According to another feature of the present invention, the coupling portion includes an arched or curved plate which is secured to the lower talus-proximal end of the shaft. This arched plate has a comparably large area for transmission of forces into the talus so that comparably small contact pressure is experienced in the area of force transmission. Preferably, the coupling portion includes an adapter having a lower end which terminates in the arched plate and is detachably secured to the shaft. With such an adapter the entire endoprosthesis can be precisely suited to the required length between the knee joint, on the one hand, and the ankle joint, on the other hand.

According to still another feature of the present invention, the adapter has a talus-distal upper end which engages a guide sleeve fixed to the shaft. This type of attachment ensures an accurate guidance of the adapter when transmitting relatively substantial bending moments.

Preferably, a template is secured to the sleeve for guiding the adapter in longitudinal direction, with the template extending in parallel relationship to the adapter. In this manner, the adapter is supported along its entire length by the template, thereby further promoting a precise guidance of the adapter while preventing a loosening thereof even when subject to substantial impact forces. Suitably, the template and the adapter have coextensive mating surfaces, thereby further enhancing the guidance of the adapter and preventing detachment from the template. The mating between the coextensive surfaces of the template and the adapter may be effected by way of a positive engagement or interference fit.

According to still another feature of the present invention, the adapter and the template define a common cross section which substantially corresponds to a cross section of the shaft. This ensures that the force-transmitting cross section of the endoprosthesis is the same over its entire length to avoid areas prone to fracture or flexure.

Suitably, the guide sleeve is attached to the shaft at a region in which the shaft is not covered by bony components of the tibia so that the template as well as the adapter can be placed through the lower end of the tibia. Thus, muscles, tendons and ligaments can remain articulated unaltered to the bony components of the tibia.

According to yet another feature of the present invention, a guiding system is positioned between the arched plate and the talus, which supports the arched plate, for guiding the arched plate. For example, the guide system may include a projection for engagement in a complementary recess of the talus. This prevents the arched plate from sliding off the talus when subject to impacts. Thus, the endoprosthesis is accurately guided with respect to the talus.

BRIEF DESCRIPTION OF THE DRAWING

The above and other objects, features and advantages of the present invention will now be described in more detail with reference to the accompanying drawing in which:

FIG. 2 is a side view of the endoprosthesis of FIG. 1, including a femoral component, a knee joint prosthesis and a tibial component;

FIG. 3 is a frontal view of the endoprosthesis;

FIG. 4 is a side view of a locator for realizing implantation of the tibial component;

FIG. 5 is a side view of a template forming one part of a coupling portion for connecting the tibial component to the natural ankle joint;

FIG. 6 is a frontal view of joined locator and template;

FIG. 7 is a side view of the joined locator and template;

FIG. 8 is a side view of an adapter forming another part of the coupling portion;

FIG. 9 is side view of the template rotated by 90° with respect to the illustration of FIG. 5;

FIG. 10 is a frontal view of joined adapter and template after removal of the locator; and FIG. 11 is a side view of the joined adapter and template.

DETAILED DESCRIPTION OF PREFERRED EMBODIMENTS

Figure 1:
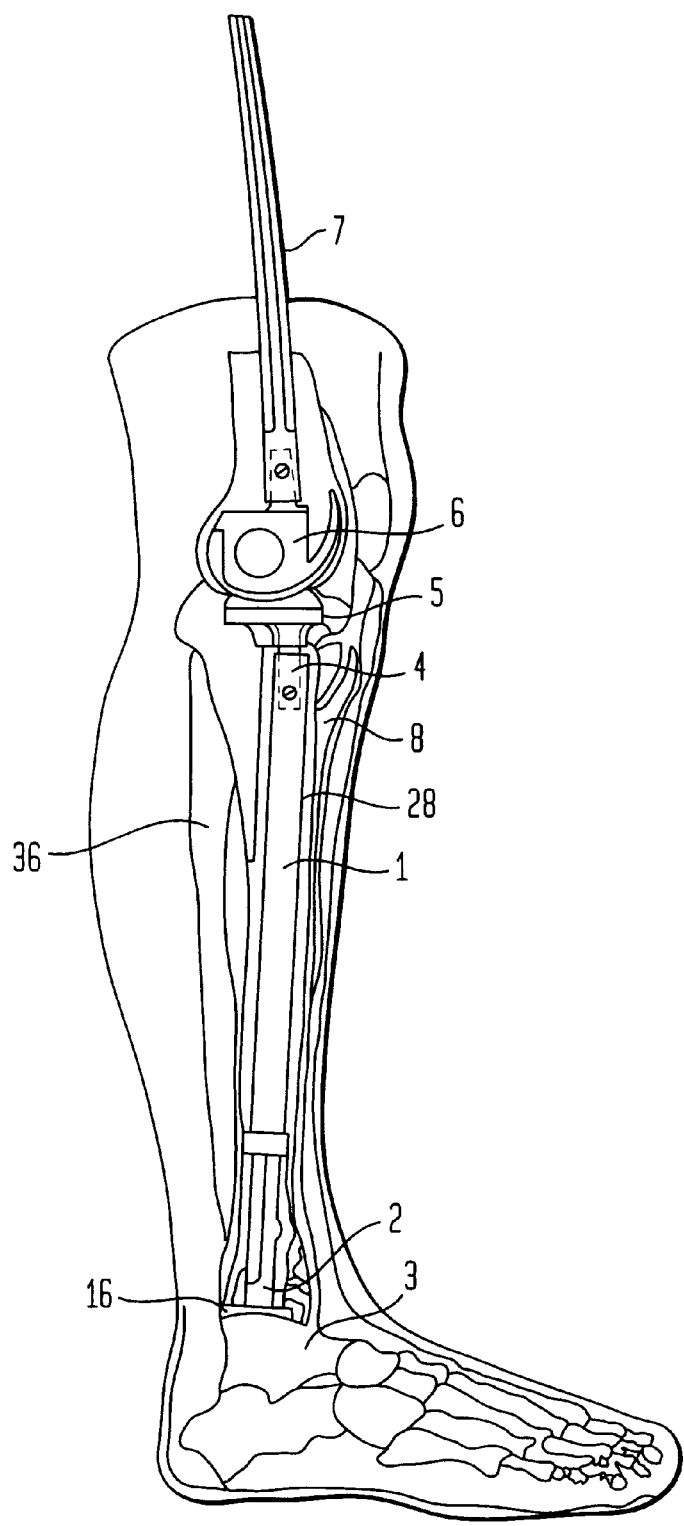
FIG. 1 is a schematic illustration of the lower part of a human leg, having implanted therein an endoprosthesis according to the present invention.

Throughout all the Figures, same or corresponding elements are generally indicated by same reference numerals.

Turning now to the drawing, and in particular to FIG. 1, there is shown a schematic illustration of the lower part of a human leg, which has a fibula 36 and a tibia 8 which is weakened to a certain extent though disease and to be replaced in part by an endoprosthesis according to the present invention. Although in the nonlimiting example of FIG. 1, parts of the tibia 8 are still existent, it is to be understood that the endoprosthesis according to the present invention is applicable also in those cases where the tibia is intended for complete replacement.

The endoprosthesis for partial replacement of the tibia 8 is comprised essentially of a shaft 1, a coupling portion 2 for attachment of a lower end of the shaft 1 to an ankle joint or talus 3 as well as an attachment 4 of the tibial plateau 5 of a endoprosthetic knee joint 6 to an upper end 9 of the shaft 1. In addition, the endoprosthesis may include a femoral prosthesis 7 which is connected to the knee joint 6 on the side distant to the tibial plateau 5. The shaft 1 extends longitudinally from the attachment 4 for the tibial plateau 5 through the tibia 8 in direction to the talus 3.

FIGS. 2 and 3 show the endoprosthesis according to the present invention in more detail. The shaft 1 may be made of a round rod, with the upper end 9 positioned adjacent to the tibial plateau 5 and formed with a recess 10 which tapers in direction of the talus 3. Received in the recess 10 is a pin 12 which is affixed to a shaft-proximal underside 13 of the tibial plateau 5. Suitably, the tibial plateau 5 is formed with transitional surfaces 14 extending from the underside 13 for improving the introduction of forces from the tibial plateau 5 into the shaft 1. Securement of the pin 12 within the recess 10 is effected by means of a screw 15 which extends transversely to the longitudinal direction of the shaft 1 through the shaft 1 as well as through the pin 12. Certainly, it is also possible to positively secure the pin 12 within the recess 10.

As shown in more detail in FIG. 8, the coupling portion 2 for connection of the shaft 1 to the talus 3 substantially includes an adapter 17 which terminates at its lower end 11 in an arched or curved plate 16 and is secured to the lower end of the shaft 1, with the arched plate 16 defining the lower extremity of the endoprosthesis for connection to the talus 3. The upper end 18 of the adapter 17 is formed with rounded edges 21 and is received in a guide sleeve 19 which, as shown in FIG. 9, forms an entry opening 20 in the direction of the talus 3 for engagement of the upper end 18 of the adapter 17, whereby the entry opening 20 has a contour which complements the outline of the upper end 18 with the rounded edges 21. The adapter 17 has a guide surface 22 by which the adapter 17 is guided on a mating surface 23 of a template 24 when the upper end 18 is engaged in the entry opening 20. The template 24 is securely fixed to the sleeve 19 and is provided to guide the adapter 17 during implantation of the endoprosthesis, with the surfaces 22, 23 positively engaging one another. A screw fastener 25 extends through the adapter 17 for threaded engagement in the template 24, thereby joining the surfaces 22, 23 to one another. In this manner, the adapter 17 is securely associated to the template 24, as shown in FIGS. 10 and 11.

The template 24 and the adapter 17 form together a cross section which substantially corresponds to the cross section of the shaft 1, whereby the adapter 17 has in the area of the guide surface 22 a thickness which slightly exceeds the thickness of the template 24. On its end 26 facing the talus 3, the template 24 is rounded so as to fit precisely in a complementary rounded segment 27 of the adapter 17.

In a situation, such as shown by way of example in FIG. 1, where parts of the tibia 8 are still existent, a bore 28 is being drilled to extend longitudinally through the tibia 8 to guide the shaft 1 therethrough. However, the arched plate 16 of the adapter 17 has such dimensions that bar a passage through the bore 28 in the tibia 8 when implanting the endoprosthesis. Therefore, after formation of the elongate bore 28, the shaft 1 is initially guided through the bore 28 by means of a locator 29 which is used as substitution in the initial phase of implantation for the adapter 17. As shown in detail in FIG. 4, the locator 29 has a guide surface 30 which has a substantial same configuration as the guide surface 22 of the adapter 17. The locator 29 is provided with a screwed hole 31 for receiving a screw fastener (not shown) which threadably engages a thread 32 of the template 24, as indicated schematically in FIG. 5. The locator 29 differs from the adapter 17 essentially by the absence of an arched plate 16 at the talus-proximal lower end 33 which, as shown in FIG. 4, is formed by a rounded terminal piece 34. The terminal piece 34 is so dimensioned as to easily pass through the elongate bore 28 of the tibia 8, without encountering problems at the lower tibial region which is of particular slender configuration. Suitably, in order to enhance the guidance of the locator 29 on the template 24, the locator 29 is formed with an arched segment 35 which is of same configuration as the rounded segment 27 of the adapter 17 and mates with the lower end 26 (FIG. 9) of the template 24 to support the guidance of the locator 29.

Implantation of endoprosthesis according to the present invention is as follows: In the of FIG. 1, where parts of the tibia 8 still exist, the bore 28 is first drilled. The locator 29 and the template 24 are assembled together, joined by screw fastener 25, as shown in FIGS. 6 and 7, and secured to the talus-proximal end of the shaft 1. Subsequently, the shaft 1 together with the attached unit of locator 29 and template 24 is inserted through the bore 28. The screw fastener 25 is then loosened to detach the locator 29 from the template 24, whereby the locator 29 can be pulled downwardly out of the bore 28 in the direction of the talus 3. The adapter 17 is now inserted into the bore 28 from below into the position where the locator 29 used to be, whereby the rounded edge 21 on the upper end 18 of the adapter 17 is received in the complementary entry opening 20 of the guide sleeve 19 of the template 24. In this position, both the guide surfaces 22, 23 mate with one another, and the adapter 17 is screwed onto the template 24. The arched plate 16 of the adapter 17 is seated in this position on the talus 3 and suitably positionally so aligned as to realize a guidance between the arched plate 16 and the talus 3. Suitably, this guidance may be, optionally, realized by providing a groove in the talus 3 in swiveling direction of the ankle joint, with a projection extending out from the arched plate 17 to engage in this groove.

Subsequently, the tibial plateau 5 is so placed onto the upper end 9 of the shaft 1 that the pin 12 is inserted into the recess 10. The screw 15 is tightened to secure the pin 12 inside the recess 10. Thus, the tibial plateau 5 is fixed in place, and the remaining parts of the endoprosthetic knee joint 6 can now be attached thereto. The femoral component 7 can be subsequently connected to the endoprosthetic knee joint 6, if necessary.

While the invention has been illustrated and described as embodied in an endoprosthesis for at least partial replacement of a tibia, it is not intended to be limited to the details shown since various modifications and structural changes may be made without departing in any way from the spirit of the present invention.

What is claimed as new and desired to be protected by letters patent is set forth in the appended claims:

1. An endoprosthesis for replacing at least part of the tibia, comprising:
   an elongate shaft defining a longitudinal axis, said shaft having an upper end facing a knee joint and a lower end facing a natural talus;
   an endoprosthetic knee joint having a tibial plateau configured for securement to the upper end of the shaft; and
   a coupling portion supported by the talus and configured to be secured to the lower end of the shaft.

2. The endoprosthesis of claim 1 wherein the shaft is formed as round rod, said upper end of the shaft being formed with a recess for complementary engagement with a pin secured to the tibial plateau, and further comprising fastening means for securing the pin in the recess.

3. The endoprosthesis of claim 2 wherein the fastening means is a screw extending transversely to the longitudinal axis of the shaft for securing the pin in the recess.

4. The endoprosthesis of claim 2 wherein the tibial plateau has a shaft-facing undersurface, said pin being secured to the underside of the tibial plateau.

5. The endoprosthesis of claim 1 wherein the coupling portion has an end in the form of a curved plate which confronts the talus and is secured to the lower end of the shaft.

6. The endoprosthesis of claim 1 wherein the coupling portion includes an adapter having an upper end detachably secured to the lower end of the shaft and a lower end configured in the form of a curved plate in confronting disposition to the talus.

7. The endoprosthesis of claim 6 wherein the coupling portion further includes a guide sleeve which is fixed to the lower end of the shaft and receives the upper end of the adapter.

8. The endoprosthesis of claim 6 wherein the coupling portion further includes a template, extending in parallel disposition to the adapter and having a guide sleeve which is fixed to the lower end of the shaft and receives the upper end of the adapter, for realizing a proper positioning of the adapter with respect to the shaft, said template extending in parallel disposition to the adapter.

9. The endoprosthesis of claim 8 wherein the template and the adapter have coextensive surfaces which complement one another.

10. The endoprosthesis of claim 8 wherein the template and the adapter have substantially same cross sections.

11. The endoprosthesis of claim 8 wherein the template and the adapter define together a common cross section which approximates a cross section of the shaft.

12. The endoprosthesis of claim 7 wherein the guide sleeve has a talus-proximal undersurface which is formed with an entry opening matched to a cross section of the adapter for engagement of the upper end of the adapter.

13. The endoprosthesis of claim 7 wherein the sleeve has a cross section which is greater than a cross section of the shaft.

14. The endoprosthesis of claim 7 wherein the guide sleeve is secured to the shaft in an area in which the shaft is free of bony material.

15. The endoprosthesis of claim 8, and further comprising locking means for for securely joining the template and the adapter to one another.

16. The endoprosthesis of claim 15 wherein the locking means includes a screw fastener extending through aligned transverse threaded bores in the template and the adapter.

17. The endoprosthesis of claim 16 wherein the screw fastener projects through the adapter for threaded engagement in the template.

18. The endoprosthesis of claim 5 wherein the curved plate has a concave curvature.

19. The endoprosthesis of claim 5, and further comprising a guide projecting out from the curved plate for engagement in a complementary recess of a bone of the ankle joint.

* * * * *